(12) United States Patent
Shimada et al.

(10) Patent No.: US 6,475,205 B2
(45) Date of Patent: Nov. 5, 2002

(54) PULL-ON DISPOSABLE DIAPER (75) Inventors: Takaaki Shimada, Kagawa-ken (JP); Seiji Suzuki, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 0 days.

(21) Appl. No.: 09/772,573

(22) Filed: Jan. 30, 2001

(65) Prior Publication Data

US 2001/0011168 A1 Aug. 2, 2001

(30) Foreign Application Priority Data

Jan. 31, 2000 (JP) ........................................ 2000-022200

(51) Int. Cl.[7] ............................ A61F 13/15; A61F 13/20
(52) U.S. Cl. ............................ 604/385.13; 604/385.29; 604/389; 604/390; 604/396
(58) Field of Search ................... 604/385.01–385.06, 604/385.13–385.14, 385.201, 385.22, 385.24–387, 389–396, FOR 103, FOR 104

(56) References Cited

U.S. PATENT DOCUMENTS

| 3,931,666 A | 1/1976 | Karami et al. |
| 4,826,499 A | * 5/1989 | Ahr ............................ 604/389 |
| 4,911,702 A | * 3/1990 | O'Leary et al. ....... 604/385.26 |

FOREIGN PATENT DOCUMENTS

| DE | 196 54 456 | 7/1998 |
| JP | 9-253123 | 9/1997 |
| JP | 9-253124 | 9/1997 |
| JP | 10-099371 | 4/1998 |

OTHER PUBLICATIONS

Copy of European Search Report dated Oct. 11, 2001.

* cited by examiner

Primary Examiner—Dennis Ruhl
Assistant Examiner—K. M. Reichle
(74) Attorney, Agent, or Firm—Baker & Daniels (57) ABSTRACT

A pull-on disposable diaper that is provided, in a vicinity of transversely opposite side edges in a rear waist region, with fastening tape strips. The fastening tape strips are adapted to hold the diaper in its rolled up state for disposal after the diaper has been used. Each of the tape strips includes a first portion extending longitudinally of the diaper parallel to the associated one of transversely opposite side edges and a second portion branched from the first portion that extends longitudinally of the diaper. Longitudinally opposite end regions of the first portion are bonded to edges of waist- and leg-openings. The second portion includes an anchoring zone adapted to be separably anchored on the outer peripheral surface of the rolled up diaper.

8 Claims, 12 Drawing Sheets

PULL-ON DISPOSABLE DIAPER

BACKGROUND OF THE INVENTION

This invention relates to a pull-on disposable diaper provided with fastening tape to fasten the diaper in its rolled-up state for disposal after the diaper has been used.

The Japanese Patent Publication A No. 1997-253123 describes a disposable diaper comprising a topsheet, a backsheet and an absorbent core disposed between these two sheets so as to configure a front waist region, a rear waist region and a crotch region extending between these two waist regions. At the front or rear waist region the backsheet is provided on the outer surface thereof with a single strip of fastening tape adapted to secure the used diaper in its rolled-up state for disposal. More specifically, the strip of fastening tape extends circumferentially of the diaper and has its longitudinally middle portion fixed to the diaper and its longitudinally opposite end portions folded-up so that these end portions may be unfolded when it is desired to use this strip of fastening tape. The longitudinally opposite end portions are coated with pressure-sensitive adhesive by means of which these end portions are maintained in a folded-up state.

Japanese Patent Publication A No. 1997-253124 describes a disposable diaper comprising a topsheet, a backsheet and an absorbent core disposed between these two sheets so as to configure a front waist region, a rear waist region and a crotch region extending between these two waist regions. At the front or rear waist region the backsheet is provided on the outer surface thereof with fastening tape adapted to secure the used diaper in its rolled-up state for disposal.

In this prior art diaper, the fastening tape comprises at least two strips of adhesive tape extending in parallel to each other circumferentially of the diaper.

For disposal, these diapers of prior art are similar to each other in that the strip(s) of fastening tape is (are) wound around the outer peripheral surface of the diaper which has been used and rolled up from its transversely opposite side edges and fixed to the outer peripheral surface of the used diaper.

Certainly, it is possible with these diapers described in the above-mentioned Publications to hold the used diaper in its rolled-up state by securing the rolled-up diaper substantially at a middle level of the diaper. However, it is impossible for these diapers to close the waist-opening of the diaper utilizing the strip(s) of fastening tape. Even after the used diaper has been tightly rolled up from its transversely opposite side edges, the waist-opening remains free and there is concern that excretion itself or its odor might leak through the waist-opening.

SUMMARY OF THE INVENTION

It is an object of this invention to provide a pants-type disposable diaper adapted to be held in its rolled-up state for disposal without any anxiety that excretion itself or its odor might leak through the waist-opening and/or the leg-openings.

According to this invention, there is provided a pants-type disposable diaper comprising a liquid-pervious topsheet, a liquid-impervious backsheet and a liquid-absorbent core disposed between the topsheet and the backsheet to define a front waist region, a rear waist region and a crotch region extending between the front and rear waist regions. The front and rear waist regions are placed upon each other with the topsheet inside along respective transversely opposite side edges of the diaper and are bonded together to define a waist-opening and a pair of leg-openings wherein the waist-opening and the pair of leg-openings have an elastic stretchability circumferentially thereof. The diaper is provided on an outer surface of the backsheet with fastening tape strips adapted to hold the diaper in a rolled-up state thereof for disposal after the diaper has been used.

This invention further includes fastening tape strips that are provided in a vicinity of the transversely opposite side edges of at least one of the front and rear waist regions. Each of the fastening tape strips is formed by a first portion extending in parallel to the side edges longitudinally of the diaper and a second portion extending from a predetermined region of the first portion longitudinally or transversely of the diaper, the first portion having longitudinally opposite end regions thereof bonded to the diaper in a vicinity of an edge of the waist-opening and in a vicinity of an edge of a respective one of the pair of leg-openings so that at least one of an intermediate region extending between the longitudinally opposite end regions of the first portion and the second portion defines an anchoring zone adapted to be removably anchored on an outer peripheral surface of the rolled-up diaper.

In the pull-on disposable diaper according to this invention, the respective first portions of the fastening tape strips have their longitudinally opposite ends secured to the respective peripheral edges of the waist- and leg-openings in contiguousness to elastic members secured under tension to the respective peripheral edges of the waist- and leg-openings so that the respective elastic members may be stretched outward transversely of the diaper as the respective fastening tape strips are pulled outward transversely of the diaper.

The fastening tape strips can be wound and anchored on the outer peripheral surface of the rolled-up diaper to hold the diaper in its rolled-up state and tensile force generated in the respective elastic members maintain the waist-opening and the leg-openings in a closed state. As a result, there is no anxiety that these openings might loosen and excretion or its odor might leak through these openings.

According to one embodiment of the diaper, the fastening tape strips can be extended to describe curves which are convex outward transversely of the diaper. In this embodiment, the fastening tape strips can be anchored on the outer peripheral surface of the diaper more firmly than the fastening tape strips extending rectilinearly. In this way, it is avoided that the fastening tape strips anchored on the outer peripheral surface of the diaper might be unintentionally peeled off therefrom.

According to another embodiment of the diaper, in which the second portions of the respective fastening tape strips extend outward from the intermediate regions of the first portions and are folded back so that they may be unfolded outward transversely of the diaper after the diaper has been used, the second portions do not extend outward transversely of the diaper before and during actual use of the diaper. In this way, the fastening tape strips can be provided in the vicinity of the side edges of the diaper and the second portions do not obstruct handling of the diaper.

DETAILED DESCRIPTION OF THE PREFERRED EMBODIMENTS

Details of a pull-on disposable diaper according to this invention will be more fully understood from the description given hereunder with reference to the accompanying drawings.

Figure 1:
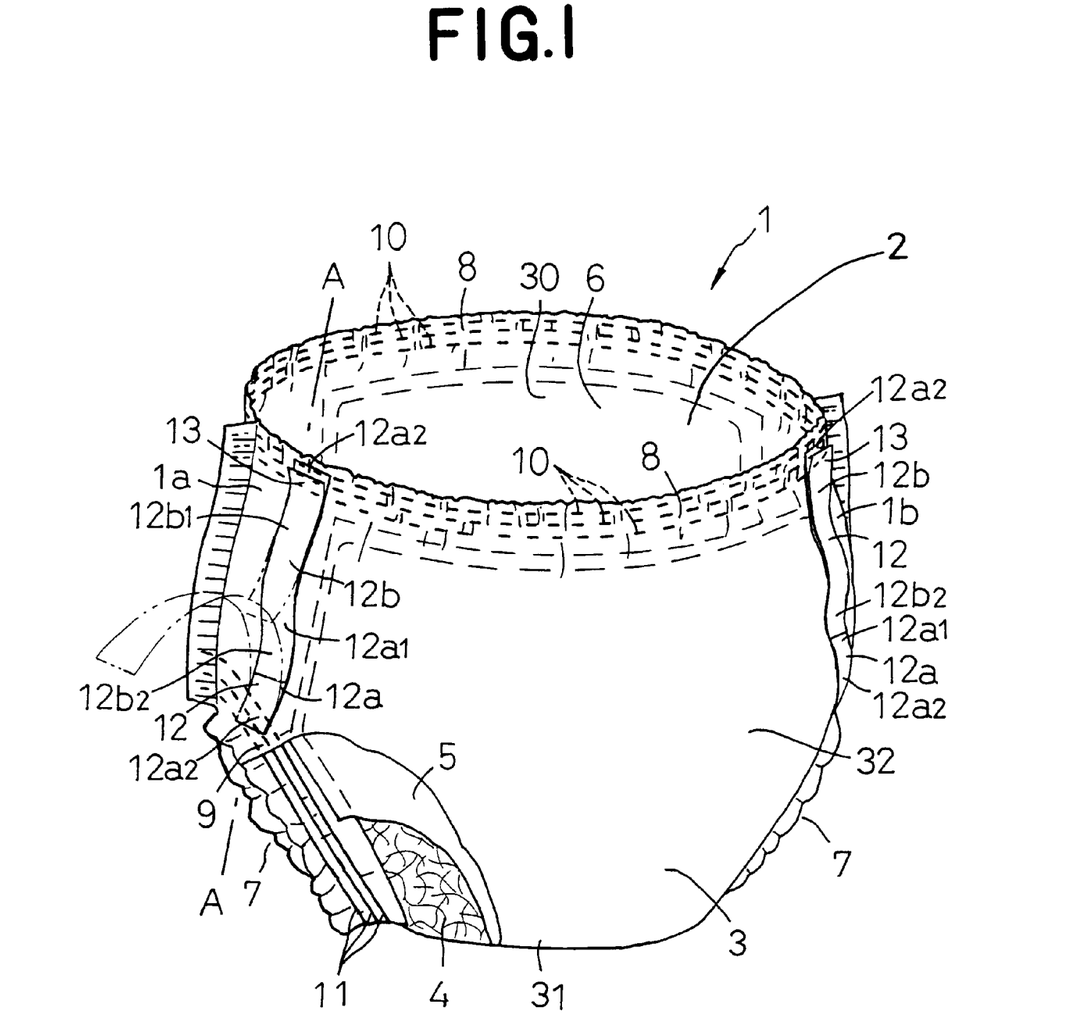
FIG. 1 is a perspective view depicting one embodiment of a partially cutaway pull-on disposable diaper according to this invention as viewed from a rear waist region side.
Figure 2:
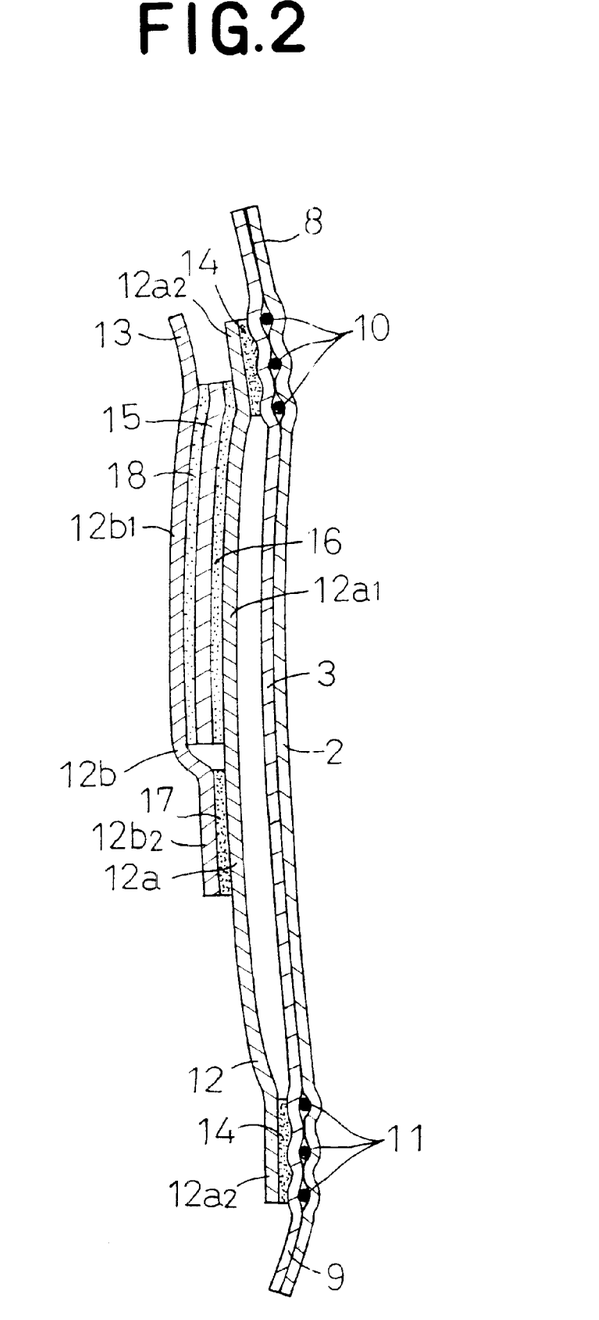
FIG. 2 is a sectional view taken along line A—A in FIG. 1.

FIG. 1 is a perspective view depicting one embodiment of a pull-on disposable diaper 1 according to this invention as viewed from the side of a rear waist region and FIG. 2 is a sectional view taken along line A—A in FIG. 1. Referring to FIG. 1, one of fastening tape strips 12 is illustrated as having been peeled off from a release sheet 15 as indicated by chain lines. The diaper 1 basically comprises a liquid-pervious topsheet 2, a liquid-impervious backsheet 3 and a liquid-absorbent core 4 disposed between the topsheet 2 and the backsheet 3 and entirely covered with and bonded to a water-pervious tissue paper 5. The tissue paper 5 is bonded to the inner surface of at least one of the topsheet 2 and the backsheet 3.

The diaper 1 is longitudinally configured by a front waist region 30, a rear waist region 32 and a crotch region 31 extending between the front and rear waist regions 30, 32. In this diaper 1, transversely opposite side edges 1a, 1b longitudinally extending in the front and rear waist regions 30, 32, respectively, are put flat together and bonded together to define a waist-opening 6 and a pair of leg-openings 7.

A plurality of elastically stretchable members 10 extend entirely along a peripheral edge 8 of the waist-opening 6 between the topsheet 2 and the backsheet 3 and are secured under tension to the inner surface of at least one of the topsheet 2 and the backsheet 3. Similarly, a plurality of elastically stretchable members 11 extend entirely along a peripheral edge 9 of each leg-opening 7 between the topsheet 2 and the backsheet 3 and are secured under tension to the inner surface of at least one of the topsheet 2 and the backsheet 3. In the diaper 1, the respective peripheral edges 8, 9 of the waist-opening 6 and the leg-openings 7 have an elastic stretchability circumferentially of these openings 6, 7. In the state shown in FIG. 1, the elastic members 10, 11 have been relieved of tension and a plurality of gathers are formed along the respective peripheral edges 8, 9 of the waist-opening 6 and the leg-openings 7.

In the vicinity of the transversely opposite side edges 1a, 1b of the rear waist region 32, the backsheet 3 is provided on its outer surface with a pair of fastening tape strips 12 that are used to hold the used diaper 1 in its rolled-up state for disposal. These fastening tape strips 12 are formed from flexible, but non-stretchable, plastic sheets each comprising a first portion 12a longitudinally extending in parallel to the side edge 1a, 1b and a second portion 12b branched from the outer surface of the first portion 12a and extending in parallel to the first portion 12a toward the peripheral edge 8 of the waist-opening 6.

The first portion 12a of each fastening tape strip 12 has longitudinally opposite end regions $12a_2$ and an intermediate region $12a_1$ extending between the longitudinally opposite end regions $12a_2$. The longitudinally opposite end regions $12a_2$ of the first portion 12a are contiguous to the elastic members 10, 11 which are, in turn, attached to the respective peripheral edges 8, 9 of the waist-opening 6 and the leg-openings 7, respectively, and bonded to the outer surface of the backsheet 3 by means of adhesive 14. While the longitudinally opposite end regions $12a_2$ are preferably contiguous to two or more of the elastic members 10, 11 respectively associated with the waist-opening 6 and the leg-openings 7, it suffices that these end regions $12a_2$ are contiguous to at least one of these elastic members 10, 11, respectively. The first portion 12a is provided on its outer surface with a plastic release sheet 15 extending from the intermediate region $12a_1$ to one of the end regions $12a_2$ and is firmly bonded to the outer surface by means of adhesive 16.

The second portion 12b of each fastening tape strip 12 is branched from the intermediate region $12a_1$ of the first portion 12a and has a fixed proximal end region $12b_2$ bonded to the outer surface of the first portion 12a by means of adhesive 17, and a free end region $12b_1$ of which the inner surface is coated with pressure-sensitive adhesive 18. The free end region $12b_1$ of the second portion 12b is removably bonded to the release sheet 15 by means of the pressure-sensitive adhesive 18. A distal end region of the second portion 12b that is free from being coated with pressure-sensitive adhesive defines a handling tip 13. Of the fastening tape strip 12, the free end region $12b_1$ of the second portion 12b is destined to be separably anchored on the outer surface of the backsheet 3 after the used diaper 1 has been rolled up for disposal.

The state of the fastening tape strip 12 is changed to the state indicated by chain lines in FIG. 1 as the free end region $12b_1$ of the second portion 12b is peeled off from the release sheet 15. Both the intermediate region $12a_1$ of the first portion 12a and the free end region $12b_1$ of the second portion 12b are deformable, e.g., flexible and twistable.

Figure 3:
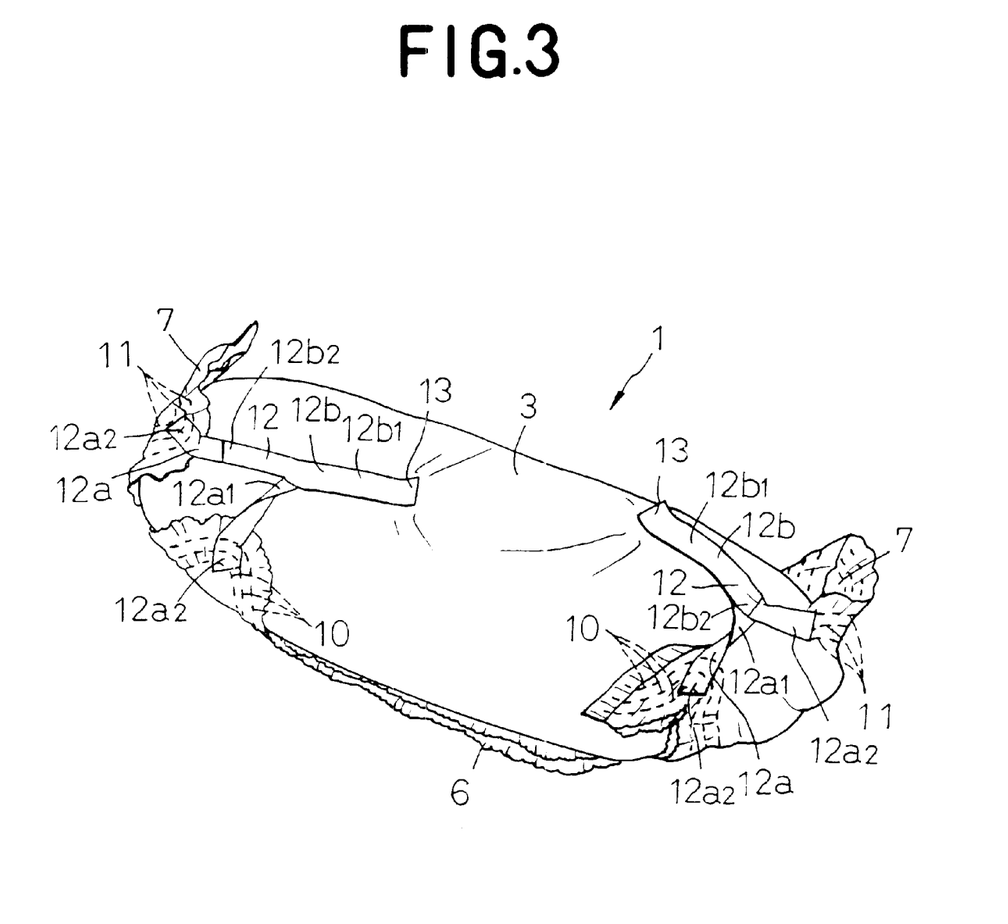
FIG. 3 is a perspective view depicting the diaper of FIG. 1 rolled up for disposal.

FIG. 3 is a perspective view depicting the diaper 1 of FIG. 1 rolled up for disposal. The diaper 1 is longitudinally rolled up from the crotch region 31 toward the waist-opening 6 with the front waist region 30 inside and the waist-opening 6 outside of the rolled-up diaper.

The first portion 12a and the second portion 12b of fastening tape strips 12 extending transversely of the diaper 1 are wound around the outer peripheral surface of the rolled-up diaper 1 and the free end region $12b_1$ of the second portion 12b is anchored on the outer surface of the backsheet 3 by means of pressure-sensitive adhesive 18. Referring to FIG. 3, the respective peripheral edges 8, 9 of the waist-opening 6 and the leg-openings 7 are partially folded inward transversely of the diaper 1.

To fasten the rolled-up diaper 1 by the fastening tape strip 12, the second portion 12b is peeled off from the release sheet 5 with the handling tip 13 held by one's fingers and then the free end region $12b_1$ of the second portion 12b is pressed against the outer surface of the backsheet 3 with the fastening tape strip 12 being pulled outward transversely of the diaper 1.

The elastic members 10 associated with the waist-opening and the elastic members 11 associated with the leg-openings to which the longitudinally opposite end regions $12a_2$ of the respective first portions 12a are attached by adhesive 14, are stretched outward transversely of the diaper 1 as the respective fastening tape strips 12 are pulled outward transversely of the diaper 1. Tensile force generated in the respective elastic members 10, 11 stretched in this manner places the respective peripheral edges 8, 9 of these openings 6, 7 under tension and thereby tends to close these openings 6, 7. In this way, the used diaper 1 is held by the respective fastening tape strips 12 in its rolled-up state and at the same time the waist-opening 6 and the leg-openings 7 are closed under the tensile force generated in the respective elastic members 10, 11. Accordingly, there is no anxiety that these openings 6, 7 might loosen and excretion or its odor might leak through these openings 6, 7.

Figure 4:
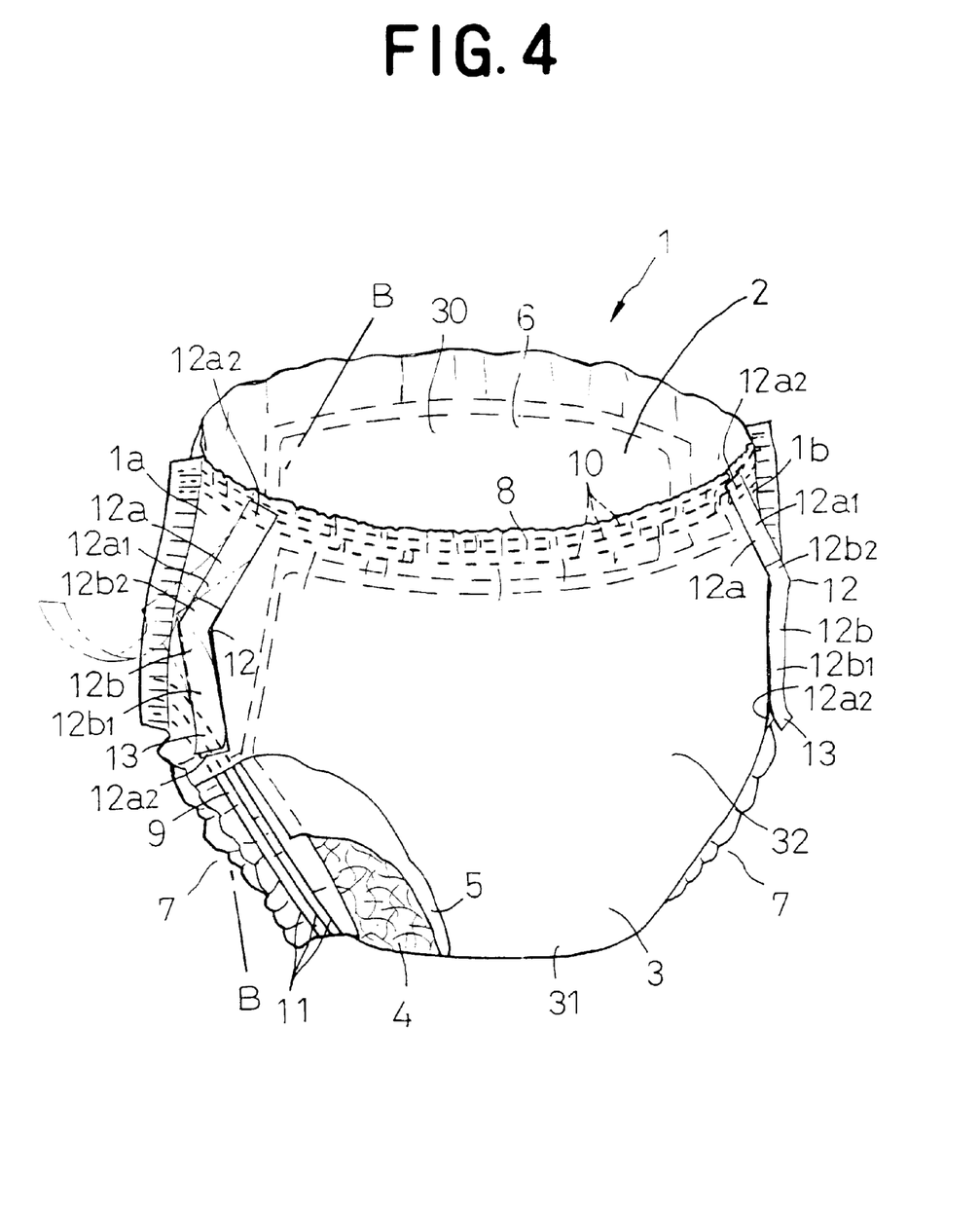
FIG. 4 is a view similar to FIG. 1 depicting another embodiment of the diaper as viewed from the rear waist region side.
Figure 5:
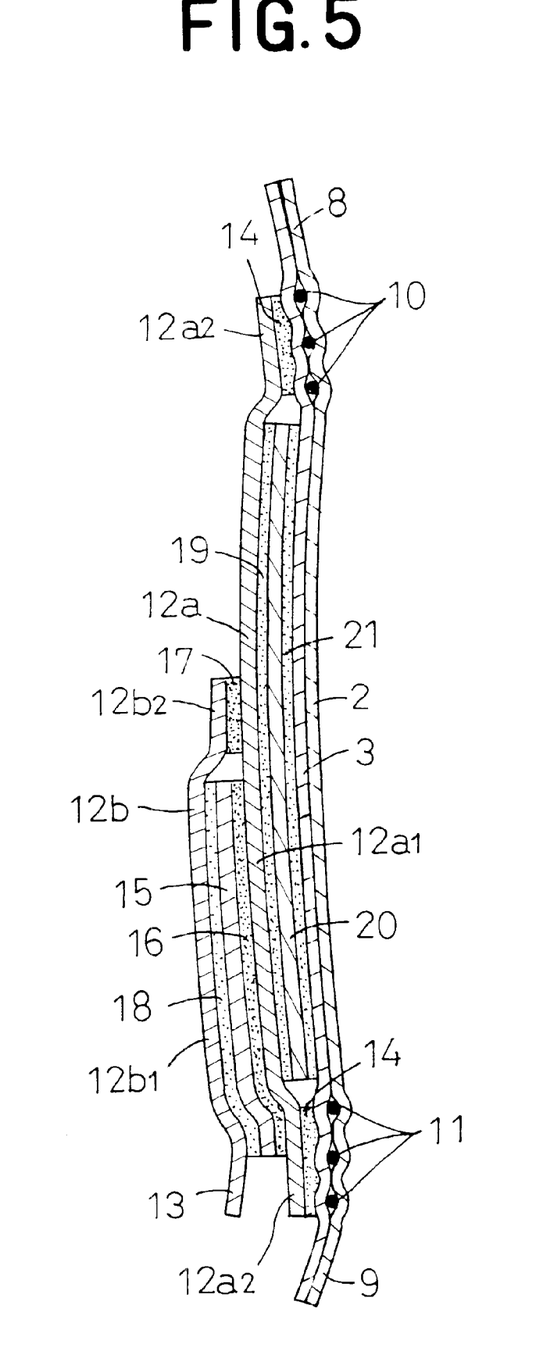
FIG. 5 is a sectional view taken along line B—B in FIG. 4.

FIG. 4 is a view similar to FIG. 1 depicting another embodiment of the diaper 1 as viewed from the side of the rear waist region 32 and FIG. 5 is a sectional view taken along line B—B in FIG. 4. Referring to FIG. 4, one of fastening tape strips 12 is illustrated as having been peeled off from release sheets 15, 20 as indicated by imaginary lines. The diaper 1 basically comprises a liquid-pervious topsheet 2, a liquid-impervious backsheet 3 and a liquid-absorbent core 4 disposed between the topsheet 2 and the backsheet 3 and covered with and bonded to a water-pervious tissue paper 5. In this diaper 1, transversely opposite side edges 1a, 1b in the front and rear waist regions 30, 32, respectively, are put flat together and firmly bonded together to define a waist-opening 6 and a pair of leg-openings 7.

A plurality of elastic members 10 are secured under tension to the waist-opening 6 along its peripheral edge 8 and a plurality of elastic members 11 are secured under tension to the leg-openings 7 entirely along their peripheral edges 9.

In the vicinity of the transversely opposite side edges 1a, 1b of the rear waist region 32, the backsheet 3 is provided on its outer surface with a pair of fastening tape strips 12. These fastening tape strips 12 are formed from flexible, but non-stretchable, plastic sheets each comprising a first portion 12a longitudinally extending in parallel to the side edge 1a, 1b and a second portion 12b branched from the outer surface of the first portion 12a and extending in parallel to the first portion 12a toward the peripheral edge 9 of the leg-openings 7.

The first portion 12a of each fastening tape strip 12 has longitudinally opposite end regions $12a_2$ and an intermediate region $12a_1$ extending to describe a curve which is convex outward transversely of the diaper 1. The longitudinally opposite end regions $12a_2$ of the first portion 12a are contiguous to the elastic members 10, 11 which are, in turn, attached to the respective peripheral edges 8, 9 of the waist-opening 6 and the leg-openings 7, respectively, and bonded to the outer surface of the backsheet 3 by means of adhesive 14.

The first portion 12a of each fastening tape strip 12 is provided on its outer surface with a plastic release sheet 15 extending from the intermediate region $12a_1$ to one of the end regions $12a_2$ and bonded to the outer surface by means of adhesive 16. The intermediate region $12a_1$ of the first portion 12a is coated on its inner surface with pressure-sensitive adhesive 19. A release sheet 20 is bonded to the outer surface of the backsheet 3 by means of adhesive 21 so that the intermediate region $12a_1$ of the first portion 12a may be removably bonded to the release sheet 20 by means of pressure-sensitive adhesive 19.

The second portion 12b of each fastening tape strip 12 is branched from the intermediate region $12a_1$ of the first portion 12a and has a fixed proximal end region $12b_2$ bonded to the outer surface of the first portion 12a by means of adhesive 17, and a free end region $12b_1$ of which the inner surface is coated with pressure-sensitive adhesive 18. The free end region $12b_1$ of the second portion 12b is removably bonded to the release sheet 15 by means of the pressure-sensitive adhesive 18. A distal end region of the second portion 12b that is free from coating of pressure-sensitive adhesive defines a handling tip 13. Of the fastening tape strip 12, the intermediate region $12a_1$ of the first portion 12a and the free end region $12b_1$ of the second portion 12b are destined to be separably anchored on the outer surface of the backsheet 3 after the used diaper 1 has been rolled up for disposal.

Figure 6:
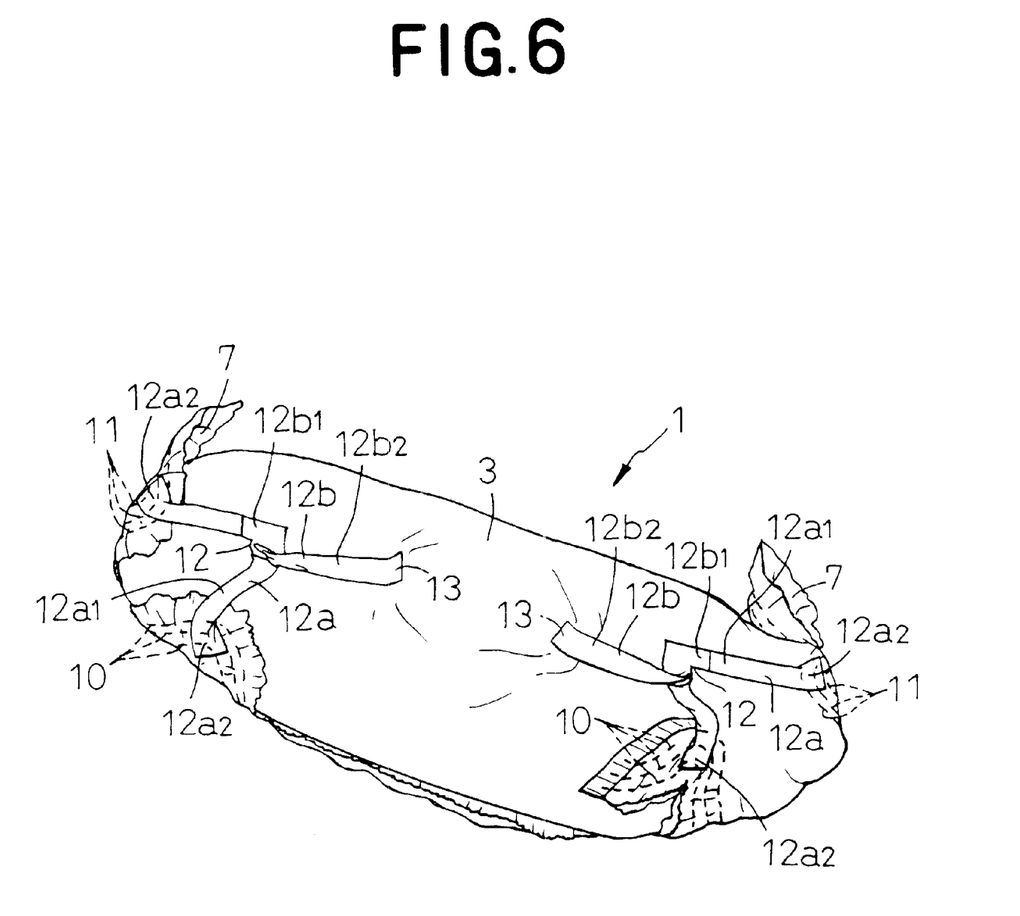
FIG. 6 is a view similar to FIG. 3 depicting the diaper of FIG. 4 rolled up for disposal.

FIG. 6 is a perspective view depicting the diaper 1 of FIG. 4 as rolled up for disposal. The diaper 1 is rolled up from the crotch region 31 toward the waist-opening 6 with the waist-opening 6 lying on the outside of the rolled-up diaper.

The first portion 12a and the second portion 12b extending transversely of the diaper 1 are wound around the outer peripheral surface of the rolled-up diaper 1. Thereupon, the intermediate region $12a_1$ of the first portion 12a and the free end region $12b_1$ of the second portion 12b have their inner surfaces anchored on the outer surface of the backsheet 3 by means of pressure-sensitive adhesive 18, 19, respectively.

Tensile force generated in the respective elastic members 10, 11 maintains the waist-opening 6 and the leg-openings 7 in a closed state and there is no anxiety that these openings 6, 7 might loosen and excretion or its odor might, leak through these openings 6, 7.

The intermediate region $12a_1$ of the first portion 12a and the free end region $12b_1$ of the second portion 12b of each fastening tape strip 12 are destined to be anchored on the backsheet's outer surface of the rolled-up diaper 1. The unique arrangement in which the first portion 12a extends so as to describe a curve which is convex outward transversely of the diaper 1 enables the intermediate region $12a_1$ of the first portion 12a to be anchored on the outer surface of the backsheet 3 more reliably than in the case in which the intermediate region $12a_1$ is not coated with pressure-sensitive adhesive or when the first portion 12a is rectilinear. Consequently, the fastening tape strips 12, once anchored on the outer surface of the backsheet 3, are prevented from being unintentionally peeled off therefrom.

Figure 7:
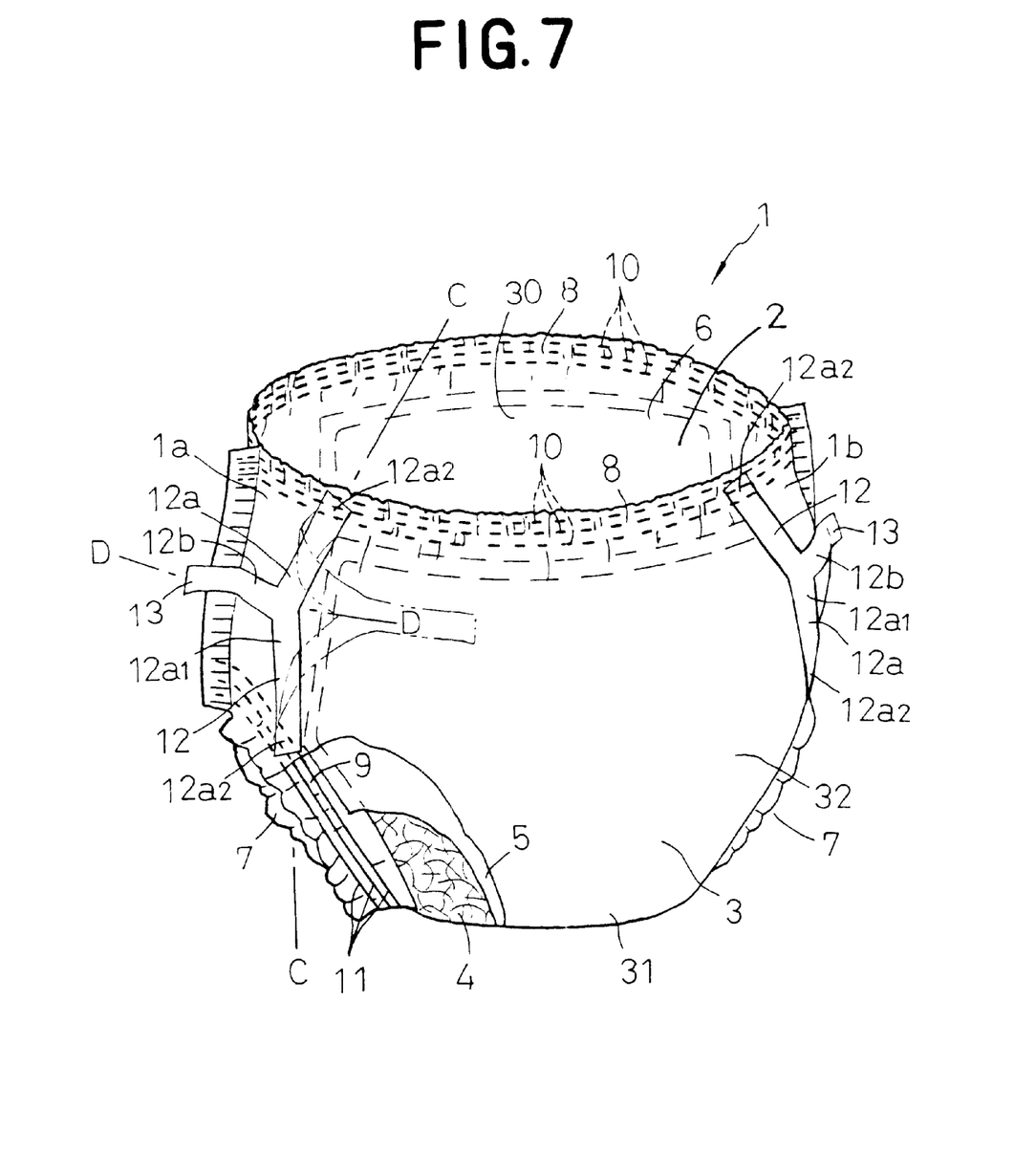
FIG. 7 is a view similar to FIG. 1 depicting still another embodiment of the diaper as viewed from the rear waist region side.
Figure 8:
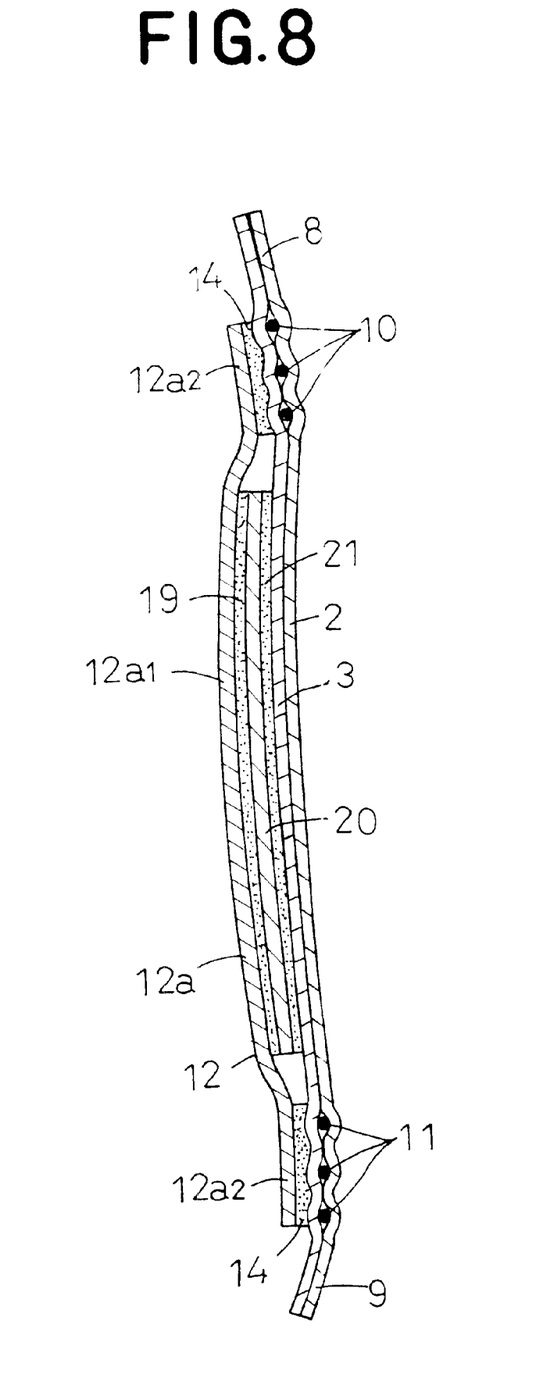
FIG. 8 is a sectional view taken along line C—C in FIG. 7.
Figure 9:
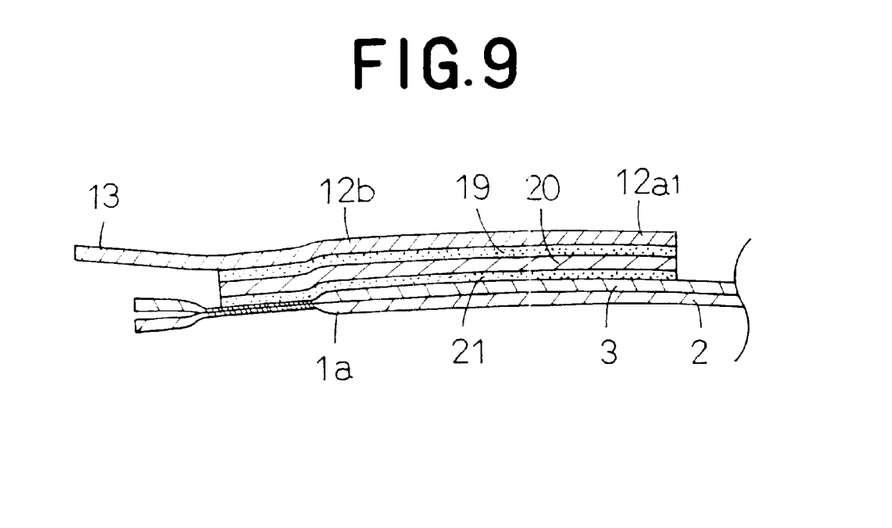
FIG. 9 is a sectional view taken along line D—D in FIG. 7.

FIG. 7 is a perspective view depicting another embodiment of the diaper 1 as viewed from the side of the rear waist region 32, FIG. 8 is a sectional view taken along line C—C in FIG. 7 and FIG. 9 is a sectional view taken along line D—D in FIG. 7. Referring to FIG. 7, one of fastening tape strips 12 is illustrated as having been peeled of from release sheet 20, as indicated by imaginary lines. The diaper 1 basically comprises a liquid-pervious topsheet 2, a liquid-impervious backsheet 3 and a liquid-absorbent core 4 disposed between the top- and backsheets 2, 3 and covered with and bonded to a water-pervious tissue paper 5. In this diaper 1, transversely opposite side edges 1a, 1b in the front and rear waist regions 30, 32, respectively, are put flat together and bonded together to define a waist-opening 6 and a pair of leg-openings 7.

A plurality of elastic members 10 are secured under tension to the waist-opening 6 along its entire peripheral edge 8 and a plurality of elastic members 11 are secured under tension to the leg-openings 7 along their entire peripheral edges 9.

In the vicinity of the transversely opposite side edges 1a, 1b of the rear waist region 32, the backsheet 3 is provided on its outer surface with a pair of fastening tape strips 12,. These fastening tape strips 12 are formed from flexible, but non-stretchable, plastic sheets each comprising a first portion 12a longitudinally extending in parallel to the side edge 1a, 1b of the diaper 1 and a second portion 12b branched from said first portion 12a.

The first portion 12a of each fastening tape strip 12 has longitudinally opposite end regions $12a_2$ and an intermediate region $12a_1$ which can be extended to describe a curve which is convex outward transversely of the diaper 1. The longitudinally opposite end regions $12a_2$ of the first portion 12a are contiguous to the elastic members 10, 11 which are, in turn, secured to the respective peripheral edges 8, 9 of the waist-opening 6 and the leg-openings 7, respectively, and bonded to the outer surface of the backsheet 3 by means of adhesive 14.

The second portion 12b of each fastening tape strip 12 extends outward transversely of the diaper 1 from the intermediate region $12a_1$ of the first portion 12a. The intermediate region $12a_1$ of the first portion 12a and the second portion 12b have their inner surfaces coated with pressure-sensitive adhesive 19. A release sheet 20 made of plastic material is bonded to the outer surface of the backsheet 3 by means of adhesive 21 so that the intermediate region $12a_1$ of the first portion 12a and the second portion 12b may be removably bonded to the release sheet 20. In this manner, the intermediate region $12a_1$ of the first portion 12a and the second portion 12b have their inner surfaces removably bonded to the release sheet 20 by means of the pressure-sensitive adhesive 19. A distal end region of the second portion 12b that is free from coating of pressure-sensitive adhesive defines a handling tip 13.

Figure 10:
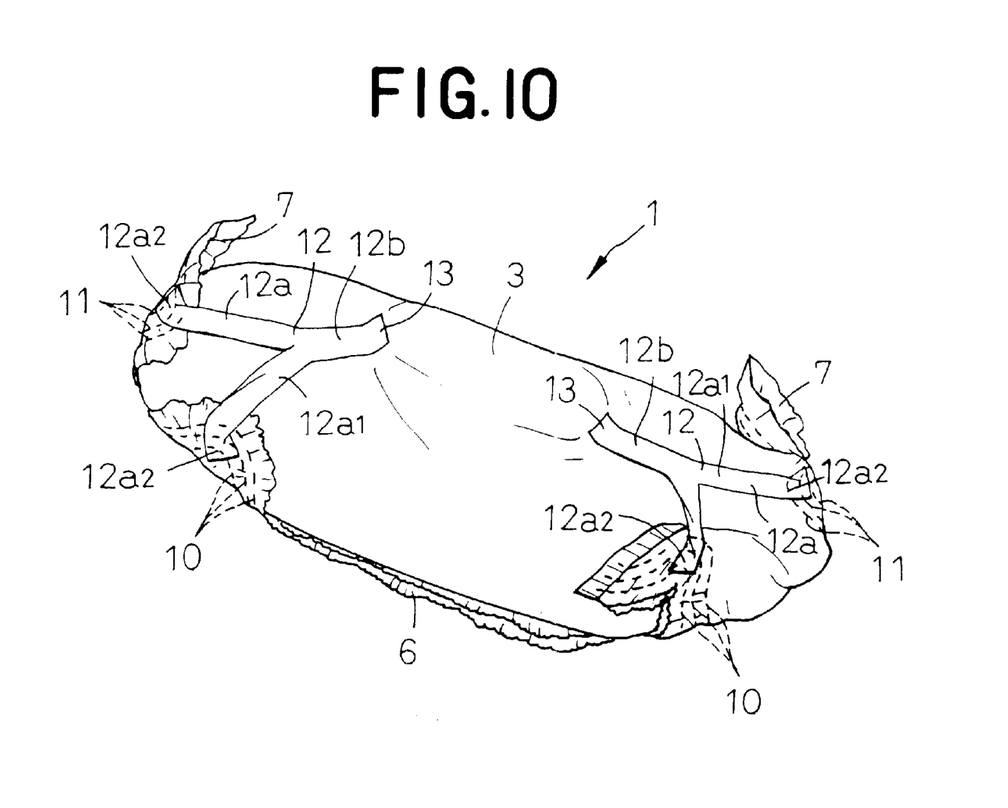
FIG. 10 is a view similar to FIG. 3 depicting the diaper of FIG. 7 rolled up for disposal.

FIG. 10 is a perspective view depicting the diaper 1 of FIG. 7 as rolled up for disposal. The diaper 1 is longitudinally rolled up from the crotch region 31 toward the waist-opening 6 with the waist-opening 6 lying on the outside of the rolled-up diaper.

The first portion 12a and, the second portion 12b of each fastening tape strip 12 extending transversely of the diaper 1 are wound around the outer peripheral surface of the rolled-up diaper 1. Thereupon, the intermediate region $12a_1$ of the first portion 12a and the second portion 12b have their inner surfaces anchored on the outer surface of the backsheet 3 by means of pressure-sensitive adhesive 19.

Tensile force generated in the respective elastic members 10, 11 maintains the waist-opening 6 and the leg-openings 7 in closed state and there is no anxiety that these openings 6, 7 might be loosen and excretion or its odor might leak through these openings 6, 7.

Figure 11:
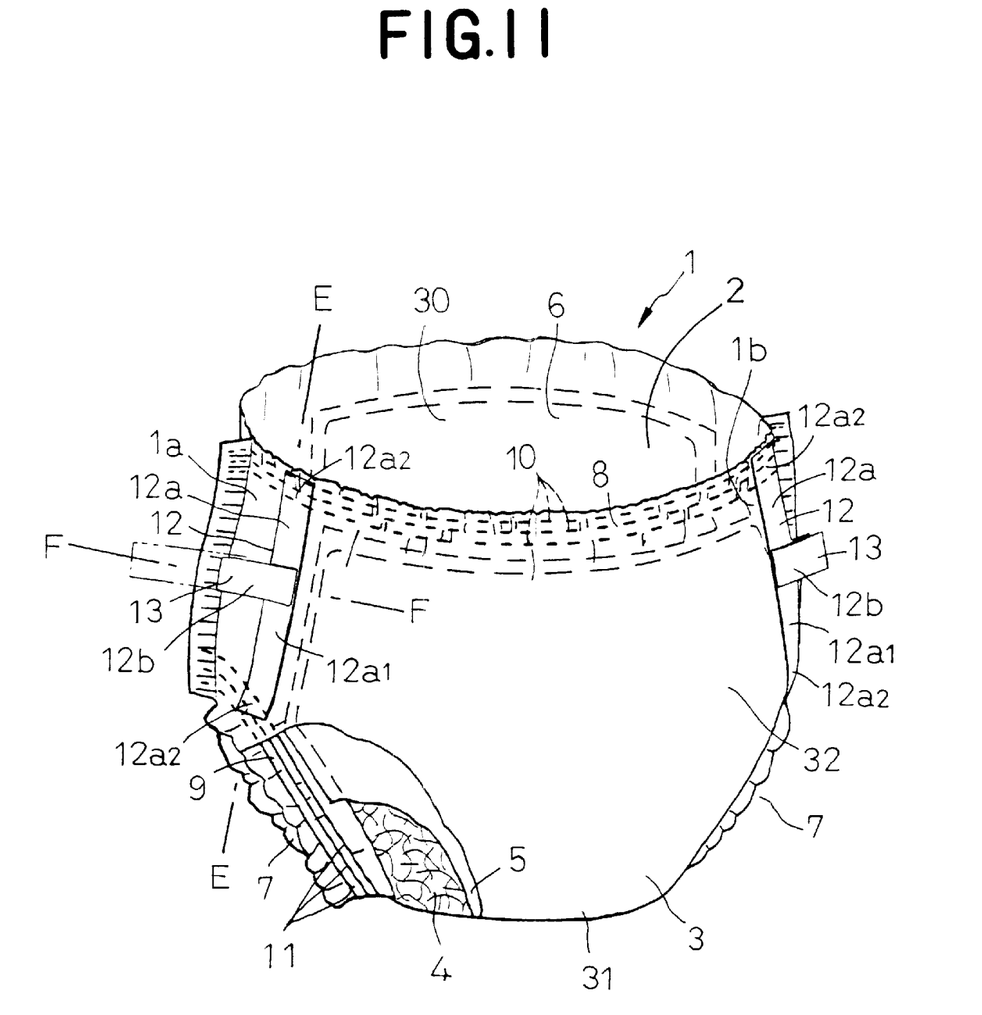
FIG. 11 is a view similar to FIG. 1 depicting further another embodiment of the diaper as viewed from the rear waist region side.
Figure 12:
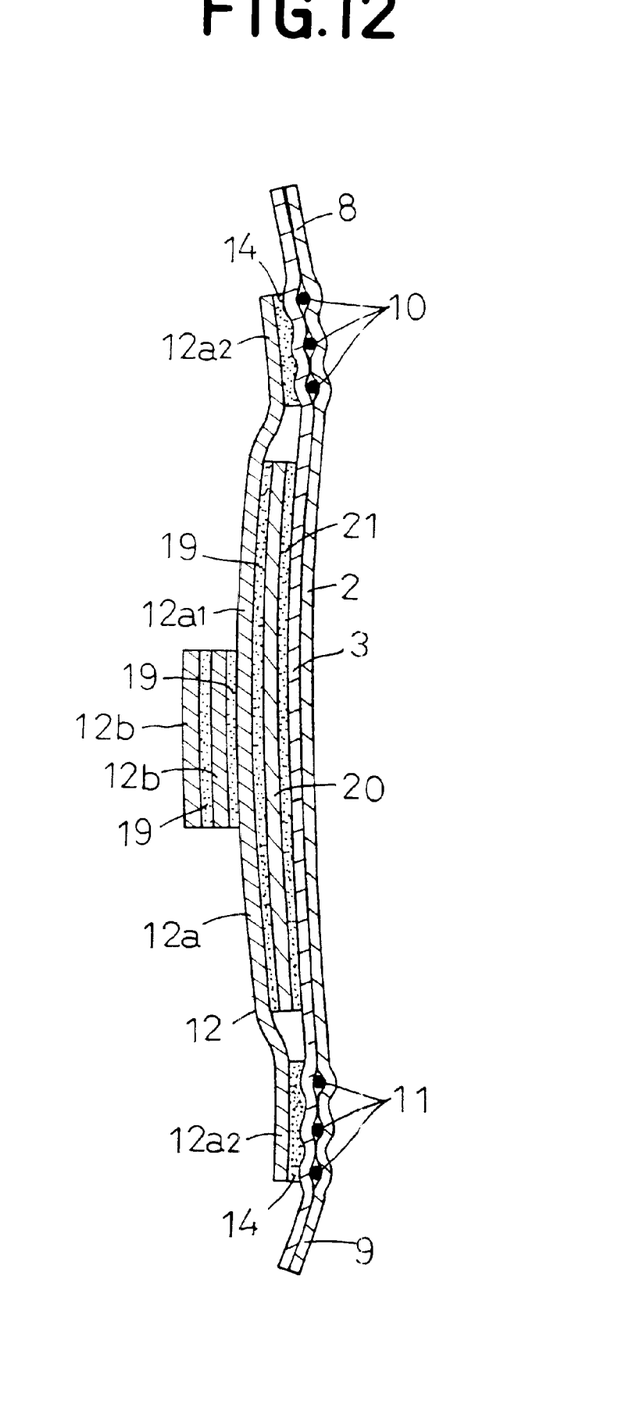
FIG. 12 is a sectional view taken along line E—E in FIG. 11.
Figure 13:
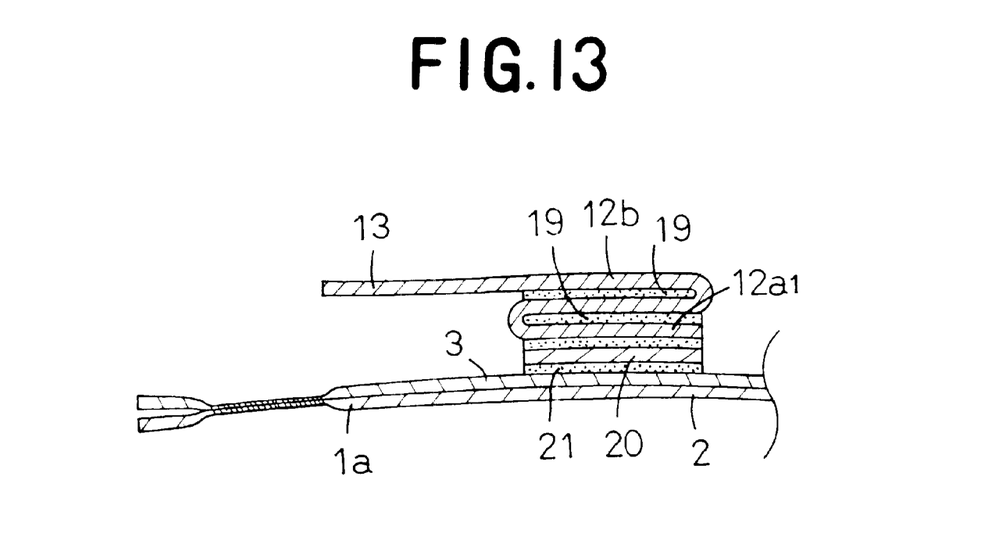
FIG. 13 is a sectional view taken along line F—F in FIG. 11.

FIG. 11 is a perspective view depicting another embodiment of the diaper 1 as viewed from the side of the rear waist region 32, FIG. 12 is a sectional view taken along line E—E in FIG. 11 and FIG. 13 is a sectional view taken along line F—F in FIG. 11. Referring to FIG. 11, one of fastening tape strips 12 is illustrated as having its second portion 12b transversely unfolded as indicated by imaginary lines. The diaper 1 basically comprises a liquid-pervious topsheet 2, a liquid-impervious backsheet 3 and a liquid-absorbent core 4 disposed between the topsheet 2 and the backsheet 3 and covered with and bonded to a water-pervious tissue paper 5. In this diaper 1, transversely opposite side edges 1a, 1b in the front and rear waist regions 30, 32, respectively, are put flat together and bonded together to define a waist-opening 6 and a pair of leg-openings 7.

A plurality of elastic members 10 are secured under tension to the waist-opening 6 along its entire peripheral edge 8 in the rear waist region 32 and a plurality of elastic members 11 are secured under tension to the leg-openings 7 along their entire peripheral edges 9.

In the vicinity of the transversely opposite side edges 1a, 1b of the rear waist region 32, the backsheet 3 is provided on its outer surface with a pair of fastening tape strips 12. These fastening tape strips 12 are formed from flexible, but non-stretchable, plastic sheets each comprising a first portion 12a longitudinally extending in parallel to the side edge 1a, 1b of the diaper 1 and a second portion 12b branched from the first portion 12a.

The first portion 12a of each fastening tape strip 12 has longitudinally opposite end regions $12a_2$ and an intermediate region $12a_1$. The longitudinally opposite end regions $12a_2$ of the first portion 12a are contiguous to the elastic members 10, 11 which are, in turn, attached to the respective peripheral edges 8, 9 of the waist-opening 6 and the leg-openings 7, respectively, and bonded to the outer surface of the backsheet 3 by means of adhesive 14.

As indicated by chain lines in FIG. 11, the second portion 12b of each fastening tape strip 12 extends outward transversely of the diaper 1 from the intermediate region $12a_1$ of the first portion 12a. The second portion 12b is folded back in half in a manner that it may be unfolded outward transversely of the diaper 1. The second portion 12b is coated in desired zones on its inner and outer surfaces with pressure-sensitive adhesive 19 so that the second portion 12b may be held in its folded state by means of the pressure-sensitive adhesive 19. The surface of the second portion 12b destined to be opposed to the pressure-sensitive adhesive 19 as the second portion 12b is folded back has previously been subjected to an appropriate surface treatment in order that the second portion 12b can be easily unfolded. A distal end region of the second portion 12b free from coating of pressure-sensitive adhesive defines a handling tip 13.

The second portion 12b of the fastening tape strip 12 may be pulled outward transversely of the diaper 1 with the handling tip 13 held by one's fingers to unfold the second portion 12b outward transversely of the diaper 1.

Figure 14:
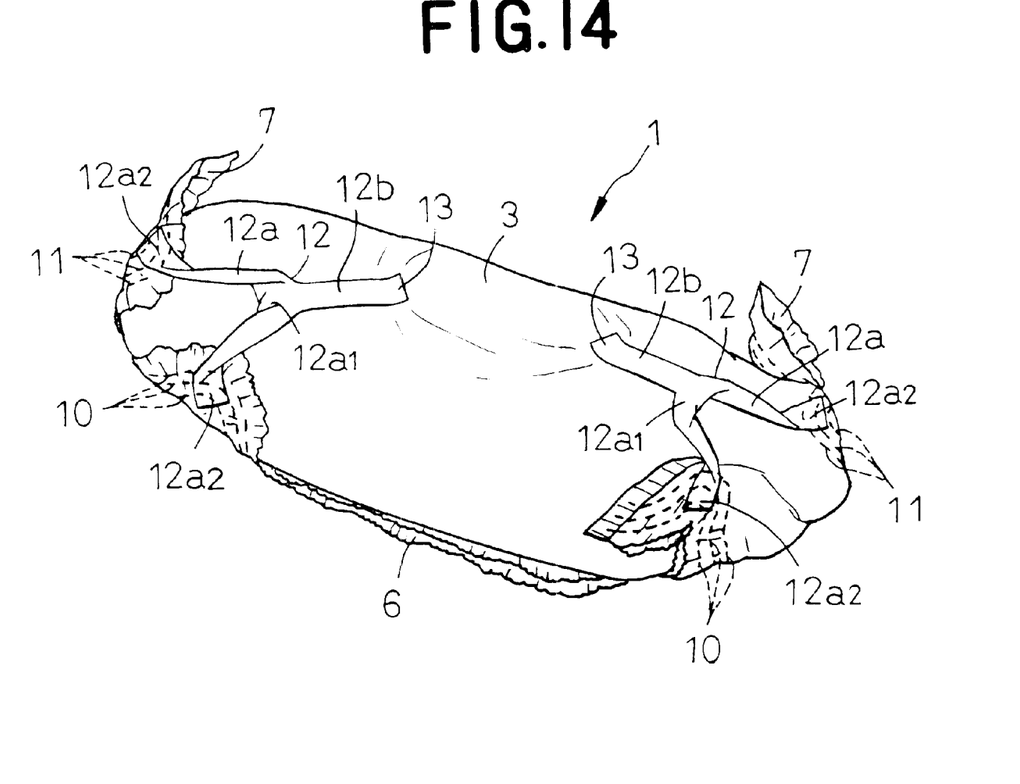
FIG. 14 is a view similar to FIG. 3 depicting the diaper of FIG. 11 rolled up for disposal.

FIG. 14 is a perspective view depicting the diaper 1 of FIG. 11 as rolled up for disposal. The diaper 1 is longitudinally rolled up from the crotch region 31 toward the waist-opening 6 with the waist-opening 6 lying on the outside of the rolled-up diaper.

The first portion 12a and the second portion 12b of each fastening tape strip 12 extending transversely of the diaper 1 are wound around the outer peripheral surface of the rolled-up diaper 1. Thereupon, the second portion 12b has its inner surface anchored on the outer surface of the backsheet 3 by means of pressure-sensitive adhesive 19.

Tensile force generated in the respective elastic members 10, 11 maintains the waist-opening 6 and the leg-openings 7 in closed state and there is no anxiety that these openings 6, 7 might loosen and excretion or its odor might leak through these openings 6, 7. The respective second portions 12b are maintained so as to be folded back in half, respectively, before and during actual use of the diaper 1 and therefore there is no concern that the handling convenience as well as the appearance of the diaper might be deteriorated by the second portions 12b extending outward transversely of the diaper 1.

The topsheet 2 may be formed from a liquid-pervious sheet such as a nonwoven fabric or porous plastic film, preferably from a liquid-pervious hydrophilic sheet. The backsheet 3 may be formed from a hydrophobic nonwoven fabric, a liquid-impervious plastic film or a laminated sheet consisting of a hydrophobic nonwoven fabric and a plastic film, preferably from a breathable liquid-impervious sheet. It is also possible to form the backsheet 3 using a composite nonwoven fabric (SMS nonwoven fabric) comprising a sheet of melt blown nonwoven fabric that is high in water resistance and two sheets of a spun bond nonwoven fabric that are high in strength as well as in flexibility so that opposite sheet surfaces of the melt blown nonwoven fabric may be sandwiched between the respective sheet surfaces of the spun bond nonwoven fabric.

The nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. Component fibers of the nonwoven fabric may be selected from a group including polyolefine fibers, polyester fibers, polyamide fibers or conjugated fibers, for example, polyethylene/polypropylene or polyester conjugated fibers.

The core 4 is a mixture of fluff pulp and high absorption polymer particles compressed to a desired thickness. Bonding or attaching of the core 4, the sheets 2, 3, 15, 20, the tape strips 12 and the elastic members 10, 11 may be accomplished using suitable adhesive such as hot melt adhesive or pressure-sensitive adhesive or heat-sealing technique.

The fastening tape strip 12 may be formed from an inelastic plastic sheet, an elastomer such as synthetic or natural rubber having a certain degree of elastic stretchability or a nonwoven fabric to which such elastomer has been secured under tension. In the case of the stretchable fastening tape strip 12, tensile force generated in the elastic members 10, 11 associated with the waist-opening and the leg-openings, respectively, cooperate with tensile force generated in the fastening tape strip 12 to improve the effect under which the waist-opening 6 and the leg-openings 7 can be held in closed state.

It is possible without departing from the scope of this invention to attach the fastening tape strips 12 to the side edges 1a, 1b of the front waist region 30, respectively. It is also possible to attach one of these fastening tape strips 12 to one side edge 1a of the diaper 1 in the rear waist region 32 and to attach the other fastening tape strip 12 to the other side edge 1b of the diaper 1 in the front waist region 30.

It is possible to dispose the longitudinally opposite end regions 12$a_2$ of the first portion 12a between the backsheet 3 and the tissue paper 5 and to bond them to at least one of the backsheet 3 and the tissue paper 5.

While the elastic members 10 associated with the waist-opening may be secured under tension to the diaper 1 along the peripheral edge 8 of the waist-opening 6 at at least one of the front and rear waist regions 30, 32, it is essential for the fastening tape strips 12 to be provided in the vicinity of the side edges 1a, 1b in the waist region provided with the elastic members 10 associated with the waist-opening 6.

In the case of the backsheet 3 formed from a nonwoven fabric, it is also possible to provide the fastening tape strips 12 with hook members instead of being coated with pressure-sensitive adhesive so that the hook members will engage with fibers of the nonwoven fabric to anchor the fastening tape strips 12 on the outer surface of the backsheet 3. When such hook members are used, loop members may be used in place of the release sheets.

What is claimed is:

1. A disposable diaper of pants-type comprising:
   a liquid-pervious topsheet;
   a liquid-impervious backsheet;
   a liquid-absorbent core disposed between said topsheet and said backsheet;
   a front waist region;
   a rear waist region; and
   a crotch region extending between said front and rear waist regions,
   said front and rear waist regions being placed upon each other with said topsheet inside along respective transversely opposite side edges of said diaper and bonded together to define a waist-opening and a pair of leg-openings, said waist-opening and said pair of leg-openings having an elastic stretchability circumferentially thereof,
   said diaper further comprising fastening tape strips for holding said diaper in a rolled up state thereof for disposal after said diaper has been used, said fastening tape strips being provided on an outer surface of said liquid-impervious backsheet in a vicinity of a respective one of said transversely opposite side edges of at least one of said front and rear waist regions,
   each of said fastening tape strips comprising a first portion extending in parallel to said side edges longitudinally of said diaper and a second portion extending from a predetermined region of said first portion longitudinally or transversely of said diaper, said first portion having longitudinally opposite end regions thereof bonded to said diaper in a vicinity of an edge of said waist-opening and in a vicinity of an edge of said leg-opening so that at least one of an intermediate region extending between said longitudinally opposite end regions of said first portion and said second portion defines an anchoring zone that is removably anchored on an outer peripheral surface of said rolled up diaper.

2. The diaper according to claim 1, wherein said second portion of each of said fastening tape strips is branched from an outer surface of a first portion of a respective one of said fastening tape strips at the intermediate region of said respective one of said fastening tape strips and extends in parallel to said first portion toward an edge of said waist-opening or an edge of a respective one of said pair of leg-openings so that an anchoring zone is defined on a surface of said second portion opposed to the outer surface of said first portion and removably bonded to the outer surface of said first portion by said anchoring zone.

3. The diaper according to claim 1, wherein said anchoring zone is defined on the inner surface of the intermediate region of said first portion and said inner surface of the intermediate region of said first portion is removably bonded to the outer surface of said backsheet in the vicinity of an adjacent one of said side edges.

4. The diaper according to claim 1, wherein said second portion of each of said fastening tape strips is branched from an intermediate region of a first portion of a respective one of said fastening tape strips and extends outward transversely of the diaper and a respective anchoring zone is defined on at least one of an inner surface of the intermediate region of said first portion and an inner surface of a second portion of a respective one of said fastening tape strips so that the inner surface of at least one of said first portion and said second portion is removably bonded to the outer surface of said backsheet in a vicinity of an adjacent one of said transversely opposite side edges by said anchoring zone.

5. The diaper according to claim 4, wherein said second portion of each of said fastening tape strips is folded back enabling said second portion to be unfolded outward transversely of said diaper, and said second portion is held in the folded back state by an anchoring zone which is defined at a predetermined region on an outer surface of said second portion.

6. The diaper according to claim 1, wherein a respective intermediate region of said first portion of each of fastening tape strips can be extended to describe a curve which is convex outward transversely of the diaper.

7. The diaper according to claim 1, wherein said fastening tape strips are made of a flexible but non-stretchable plastic sheet.

8. The diaper according to claim 1, wherein each anchoring zone is coated with a pressure-sensitive adhesive.

* * * * *